(12) United States Patent
Ruettinger et al.

(10) Patent No.: US 8,343,885 B2
(45) Date of Patent: Jan. 1, 2013

(54) ISOMERIZATION CATALYSTS

(75) Inventors: Wolfgang Ruettinger, East Windsor, NJ (US); Ahmad Moini, Princeton, NJ (US); Bala Ramachandran, Easton, PA (US); Sukwon Choi, Clifton, NJ (US)

(73) Assignee: BASF Corporation, Florham Park, NJ (US)

( * ) Notice: Subject to any disclaimer, the term of this patent is extended or adjusted under 35 U.S.C. 154(b) by 129 days.

(21) Appl. No.: 12/974,176

(22) Filed: Dec. 21, 2010

(65) Prior Publication Data

US 2012/0157294 A1 Jun. 21, 2012

(51) Int. Cl.
*B01J 23/00* (2006.01)
*B01J 21/00* (2006.01)
*B01J 37/00* (2006.01)
*B01J 29/00* (2006.01)
*B01J 20/00* (2006.01)

(52) U.S. Cl. ............ 502/73; 502/84; 502/242; 502/251; 502/302; 502/303; 502/304; 502/340; 502/349

(58) Field of Classification Search .................... 502/73, 502/84, 242, 251, 302–304, 340, 349
See application file for complete search history.

(56) References Cited

U.S. PATENT DOCUMENTS

| | | |
|---|---|---|
| 4,684,760 A | 8/1987 | Drake |
| 4,754,098 A | 6/1988 | Drake |
| 4,889,840 A | 12/1989 | Drake |
| 5,134,103 A | 7/1992 | Lowery et al. |
| 5,153,165 A | 10/1992 | Lowery et al. |
| 5,300,718 A | 4/1994 | McCaulley |
| 6,762,433 B2 | 7/2004 | Yamaguchi |
| 6,875,901 B2 | 4/2005 | Gartside et al. |
| 7,518,023 B2 * | 4/2009 | Geyer et al. .................... 585/250 |
| 7,652,087 B2 * | 1/2010 | Dimanshteyn et al. ........ 524/430 |
| 8,263,518 B2 * | 9/2012 | Khare .............................. 502/66 |
| 2003/0004385 A1 | 1/2003 | Gartside et al. |
| 2003/0017631 A1 | 1/2003 | Yamaguchi |
| 2008/0057267 A1 | 3/2008 | Brocheton et al. |
| 2009/0281360 A1 | 11/2009 | Knowles et al. |
| 2010/0056839 A1 | 3/2010 | Ramachandran et al. |
| 2010/0233487 A1 | 9/2010 | Millero et al. |

FOREIGN PATENT DOCUMENTS

| | | |
|---|---|---|
| EP | 0211985 | 3/1987 |
| EP | 0354584 | 2/1990 |
| EP | 1854776 | 11/2007 |
| WO | WO-02/096843 | 12/2001 |
| WO | WO-02/094433 | 11/2002 |

* cited by examiner

*Primary Examiner* — Cam N. Nguyen
(74) *Attorney, Agent, or Firm* — Bernard Lau

(57) ABSTRACT

Extruded isomerization catalysts comprising MgO, a metal silicate clay binder and a stabilizer and methods of forming such isomerization catalysts are disclosed. Also disclosed are isomerization catalysts that exhibit a fresh isomerization rate and an aged isomerization rate that is at least 50% of the fresh isomerization rate. Embodiments of the isomerization catalysts disclosed herein include metal silicate clay binders that include a layered structure and metal silicate. The metal silicate clay binder may be present in an amount in the range from about 5 wt % to about 20 wt %. Exemplary stabilizers include one or more of $ZrO_2$, tetravalent rare earth metal and a trivalent rare earth metal. Stabilizers may be present in an amount up to about 40 wt %. One or more improved properties, such as piece crush strength and isomerization performance, are exhibited by the catalyst article.

20 Claims, 1 Drawing Sheet

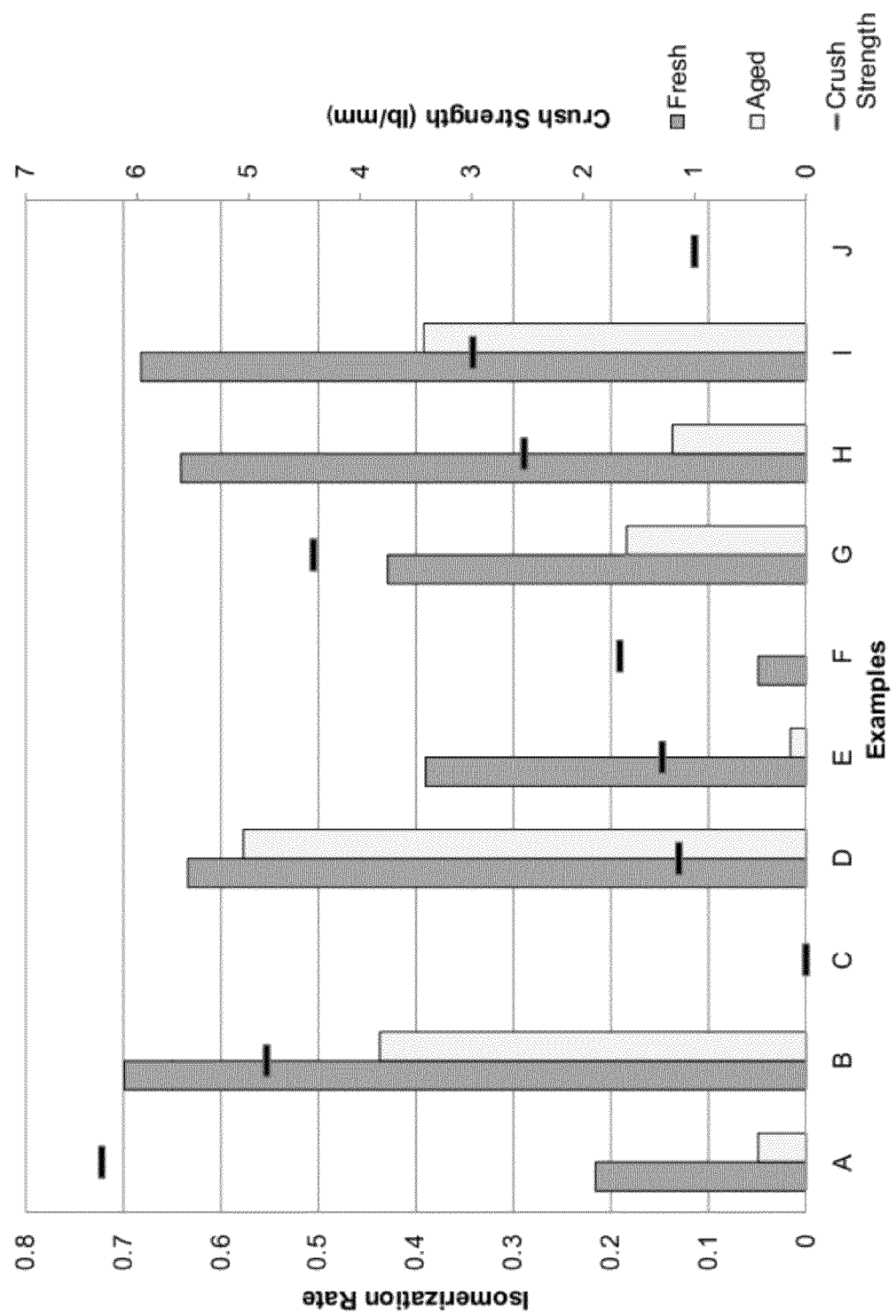

ISOMERIZATION CATALYSTS

TECHNICAL FIELD

Embodiments of the present invention are directed to isomerization catalysts and methods of their manufacture. More specifically, embodiments of the present invention are directed to 1-butene isomerization catalysts comprising MgO, a metal silicate clay binder and a stabilizer.

BACKGROUND

MgO tablets are used as a co-catalyst in the metathesis reaction of butene with ethylene to form propylene. The metathesis reaction to form propylene includes the following reactions:

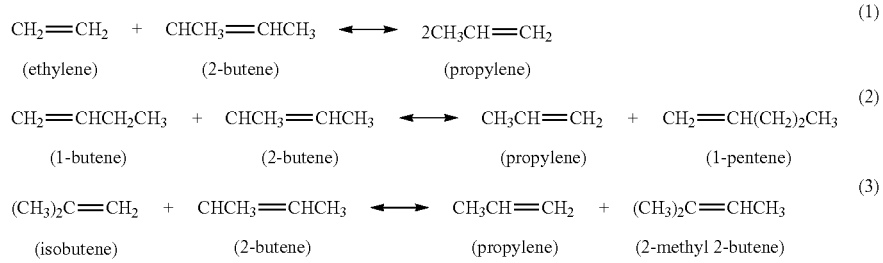

MgO accomplishes the isomerization of 1-butene to 2-butene and adsorbs poisons in the feed stream such as $H_2O$, $CO_2$, oxygenates (such as methyl tertiary butyl ether or MTBE), sulfur compounds, nitrogen compounds, heavy metals and the like.

Isomerization catalysts in tablet form exhibit a crush strength that permits the catalyst to withstand the pressures and stress that are exerted on the catalysts during use. However, the manufacture of tablets is costly and time consuming. In addition, the formation of tablets having complex shapes is difficult or not possible.

Accordingly, there is a need for an isomerization catalyst that can be provided in a different form from tablets and that maintains an acceptable isomerization activity after aging. There is also a need for isomerization catalysts that exhibit acceptable crush strength so the catalyst can withstand the pressure of hydrocarbon flow in the catalyst system as well as the stress placed on the catalyst when packed into a reactor.

SUMMARY

As used herein, the term "crush strength" shall refer to single piece crush strength or piece crush strength. Crush strength may be defined as the resistance of a formed catalyst to compressive forces. Measurements of crush strength are intended to provide indication of the ability of a catalyst to maintain its physical integrity during handling and use. Piece crush strength may be measured by placing an individual catalyst, whether in the form of an extrudate, tablet or otherwise, between two flat surfaces and applying a compressive load to the catalyst or through the two flat surfaces to the catalyst and measuring the force required to crush the piece using a force transducer.

One or more embodiments of the present invention pertain to a catalyst provided as an extrudate. In such embodiments, processing of MgO or $Mg(OH)_2$ is needed to form MgO into an extrudate because it is provided as a powder.

A first aspect of the present invention pertains to an extruded catalyst comprising MgO, a metal silicate clay binder and one or more of $ZrO_2$, tetravalent rare earth metal and a trivalent rare earth metal, wherein the catalyst exhibits a piece crush strength of at least 2.0 lbs/mm. In one or more embodiments, the extruded catalyst exhibits a fresh isomerization rate and an aged performance after aging at 650° C. for 24 hours, wherein the aged isomerization rate is at least 50% of the fresh isomerization rate. In one variant, the fresh isomerization rate and the aged isomerization rate of the extruded catalysts disclosed herein comprise a 1-butene to 2-butene isomerization rate.

In one or more variants, MgO is present in the extruded catalyst in an amount in the range from about 0.1 wt % to 90 wt %. In a specific embodiment, MgO may be present in an amount of at least 50 wt %. Alternatively, MgO may be present in the range from about 70 wt % to about 90 wt % or, more specifically, an amount of about 80 wt %.

Suitable metal silicate clay binders may include layered particles having an aspect ratio of diameter to thickness in the range of 25 to 50 and strong negative charges on faces of the particles and weak positive charges on edges of the particles. In one or more embodiments, the metal silicate clay binder may include a synthetic metal silicate. In one variant, the synthetic metal silicate clay binder comprises a synthetic hectorite.

In one or more embodiments, the metal silicate clay binder may be present in an amount in the range of 1 wt % and 20 wt %. In a more specific embodiment, the metal silicate clay binder may be present in an amount in the range from about 5 wt % to about 20 wt %. In an even more specific embodiment, the metal silicate clay binder may be present in an amount in the range from about 8 wt % to about 12 wt % or may be present in an amount of about 10 wt %.

$ZrO_2$, tetravalent rare earth metal and/or a trivalent rare earth metal may be present in one or more variants of the extruded catalyst in the range of 1 wt % and 20 wt %. Examples of suitable trivalent rare earth metals include one or more of La, Ce, Pr and Nd. $ZrO_2$ may be present in the extruded catalyst in an amount up to about 40 wt %. In a more specific embodiment, $ZrO_2$ may be present in an amount in the range from about 5 wt % to about 15 wt % or, more specifically, about 10 wt %.

A second aspect of the present invention pertains to a method of forming a 1-butene isomerization catalyst. In one or more embodiments, the method may include mixing a MgO source, a metal silicate clay binder and one or more of a $ZrO_2$-precursor, a tetravalent rare earth metal and a trivalent rare earth metal to form a first mixture and adding water to the first mixture to form a second mixture. The method may also include extruding the second mixture to form an extrudate exhibiting a single piece crush strength of at least 2.0 lbs/mm and exhibiting a fresh isomerization rate and an aged performance after being aged at 650° C. for 24 hours, wherein the aged isomerization rate is at least 50% of the fresh isomerization rate.

In one embodiment, the method may utilize $ZrO_2$, tetravalent rare earth metal and a trivalent rare earth metal that are selected from one of zirconium carbonate, zirconium acetate, zirconium nitrate and combinations thereof. In one variant, metal silicate clay binder may be present in an amount in the range of about 5 wt % and 20 wt %.

In one or more embodiments, the method of forming a 1-butene isomerization catalyst may include dry-mixing the MgO source, metal silicate clay binder and one or more of $ZrO_2$, tetravalent rare earth metal and a trivalent rare earth metal. In one variant of the method, $ZrO_2$, tetravalent rare earth metal and trivalent rare earth metal may be provided in solution form.

BRIEF DESCRIPTION OF THE DRAWINGS

FIG. 1 illustrates the fresh and aged conversion of 1-butene at atmospheric pressure, WHSV=45 $h^{-1}$ and crush strength of isomerization catalysts according to embodiments of the present invention and known isomerization catalysts according to the prior art.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

A first aspect of the present invention pertains to extruded isomerization catalysts comprising MgO, a metal silicate clay binder and a stabilizer. The invention is not limited to a particular extrudate shape. Nonlimiting examples of shapes that can be formed by extrusions include cylindrical extrudates, trilobes, quadralobes, hollow cylinders, star shapes, etc. In one or more embodiments, the MgO is present in the extrudates in an amount of at least 50 wt % and up to about 90 wt %. In one or more specific embodiments, MgO is present in the extrudates in an amount in the range from about 70 wt % to about 90 wt %. In a specific embodiment, MgO may be present in an amount of about 80 wt %. MgO may be provided as a magnesium oxide powder or as magnesium hydroxide, magnesium carbonate or the like and further processed with other components to form an extrudate.

The metal silicate clay binder is provided as to accommodate the lack of binding found in MgO-containing catalysts that do not utilize metal silicate clay binders. Metal silicate clay binders have been found to sufficiently bind MgO and other components, without sacrificing or negatively affecting activity of the material in the isomerization reaction. In one or more embodiments, the metal silicate clay binder may be present in an amount in the range from about 0.1 wt % to about 40 wt %. In one variant, the metal silicate clay binder may be present in an amount in the range from about 5 wt % to about 25 wt % or, more specifically, in the range of about wt % to about 20 wt %, and even more specifically in an amount of about 10 wt %.

In one or more embodiments, metal silicate clay binders may include layered structures. In one or more specific embodiments, the metal silicate clay binders may include metal silicate and even more specific embodiments may include magnesium silicate or magnesium aluminosilicate. The metal silicate clay binder can be selected from the group: montmorillonite, saponite, nontronite, beidellite, smectites (including hectorite), stevensite, magadiite, mica minerals (including illite). In specific embodiments, the metal silicate clay binder is a magnesium silicate clay or a magnesium aluminum silicate clay. In more specific embodiments, the metal silicate clay binder is a smectite, and in more specific embodiments, the metal silicate clay binder is a hectorite. In even more specific embodiments, the metal silicate clay binder is a synthetic clay binder, more specifically, a synthetic hectorite clay binder, and even more specifically, Laponite®. Synthetic metal silicate clay binders may be preferable because certain impurities in natural clays may negatively influence performance, however, embodiments of the invention include natural clays to the extent the rheological properties of the extrudate mixture are not adversely impacted. The clay nanoparticles (C) may have an average particle diameter of 5-500 nm, preferably 5-100 nm, more preferably 5-50 nm. Laponite® is a synthetic, disc-shaped silicate, with a thickness of approximately 1 nm and a diameter of 25 nm. In aqueous dispersions, Laponite® has a strongly negative charge on its faces and a weakly localized positive charge on its edges. The surface charges on such nanoparticles cause the formation of electrical double layers e.g. of Na+ ions in aqueous solution. Thus, according to one aspect of the invention, the metal silicate clay binder is a metal silicate clay binder having an aspect ratio of diameter to thickness in the range of about 25 to about 500, more specifically, of about 25 to 100, and even more specifically of about 25 to 50. In one or more embodiments, the clay binder having such aspect ratios has a strong negative face charge and a weak local positive charge on its edges. Laponite® binders are available under the tradename Laponite®, from Rockwood Additives Ltd. of Cheshire, UK. As will be discussed in more detail below, metal silicate clay binders function as sufficient binders without substantially adversely affecting the crush strength or the activity of the catalysts.

The layered structure of one or more suitable examples of metal silicate clay binders includes disc-shaped crystals as described above that are capable of forming a "house of cards" structure when dispersed in water and other additives to form a gel. In the "house of cards" structure the disc-shaped particles include a face and an edge, wherein the face has a different electrical charge than the edge. In one or more embodiments, the edge of the particle has a small localized positive charge, while the face has a negative charge. Accordingly, when added to an aqueous solution under proper conditions (for example, in absence of salts or surfactants), the weaker positive charge on the edge of the particles interact with the negative faces or face surfaces of adjacent particles, thus forming a house of cards structure to provide a highly thixotropic gel. The "house of cards" structure can also be broken down or dispersed under shear stress but reform when the shear stress is removed. Therefore, the material becomes fluid under the shear in an extruder, but forms a stable structure after extrusion and drying.

The extruded catalyst of one or more embodiments may include a stabilizer. In one or more embodiments, the stabilizer may include $ZrO_2$, tetravalent rare earth metal, a trivalent rare earth metal and combinations thereof. In one or more embodiments, the stabilizer excludes or is substantially free of any intentionally added $SiO_2$ and/or $Al_2O_3$. The stabilizer may be present in one or more embodiments in an amount in the range from about 5 wt % to about 40 wt %. In one variant, the stabilizer may be present in an amount in the range from about 5 wt % to about 20 wt %, or more specifically, about 10 wt %.

One or more embodiments of the present invention may incorporate $ZrO_2$ as a stabilizer. In one or more variants, $ZrO_2$ may be provided in solution form. For example, $ZrO_2$ may be provided as zirconium carbonate, zirconium acetate and zirconium nitrate and other known zirconium-containing solutions. In such embodiments, the zirconium-containing solutions are provided with the remaining components to provide an extrudate with a stabilizer comprising $ZrO_2$. In one or more embodiments, $ZrO_2$ may be provided in solid form such as a powder or a paste. As such, zirconium may be added in the form of a hydrous oxide or hydroxide or as a zirconium carbonate powder or paste. $ZrO_2$ may be present in an amount up to about 40 wt %. In one variant, $ZrO_2$ may be present in an amount in the range from about 5 wt % to about 15 wt %, or more specifically, in an amount of about 10 wt %.

Examples of trivalent and tetravalent rare earth metals that may be utilized include cerium, praseodymium, neodymium and lanthanum.

Embodiments of the isomerization catalysts described herein may be utilized to convert 1-butene to 2-butene. In one or more embodiments, the isomerization catalysts described herein maintain at least a pre-determined isomerization rate after aging. For example, isomerization catalysts described herein may exhibit a fresh isomerization rate and an aged isomerization rate that is at least 50% of the fresh isomerization rate. Aging of the catalyst occurs when the material is used for long periods of time and regenerated repeatedly in the process. In an accelerated aging procedure, the catalyst is therefore exposed to a temperature of 650° C. in static air for a period of 24 hours. In one or more specific embodiments, the isomerization catalysts described herein exhibit an aged isomerization rate of at least 60% of the fresh isomerization rate, or more specifically at least 65% of the fresh isomerization rate.

In one or more embodiments, the isomerization catalysts described herein exhibit a piece crush strength of at least 1.5 lbs/mm (0.68 kg/mm). In one or more embodiments, the isomerization catalysts exhibit a piece crush strength of at least 2.0 lbs/mm (0.91 kg/mm) or at least 2.5 lbs/mm (1.13 kg/mm). As used herein, the term "crush strength" shall include the resistance of formed catalysts to compressive forces. In other words, the catalysts exhibit a crush strength that provides an indication of the ability of the catalyst to maintain its physical integrity during handling and use. In the embodiments described herein, piece crush strength was measured by placing a cyclindrical individual catalyst piece between dies having area width of about 0.125 in (3 mm). The force required to crush the piece between the dies was measured by force transducer.

The isomerization catalysts described herein are extruded or provided as extrudates. Known isomerization catalysts have been provided in tablet form, however, the formation of tablets has been found to be costly and time consuming. The geometry of tableted catalysts is further limited. Extruding isomerization catalysts have provided a more efficient and cost effective alternative, which provides isomerization catalysts that exhibit the desired piece crush strength and isomerization rate after aging. Moreover, extrudates offer the ability to provide different geometries, which can improve or otherwise affect crush strength and isomerization activity. In one or more embodiments, the isomerization catalysts described herein may have a diameter in the range from about 0.375 inches (9.525 mm) to about 0.0625 inches (1.5875 mm).

A second aspect of the present invention pertains to methods of forming the isomerization catalysts described herein. In one or more embodiments, the Mg-compound, binder and stabilizer are mixed to form a first mixture. Water may be added to the second mixture to form a second mixture, which is then extruded to form an extrudate. In one or more embodiments, the first mixture comprises a dry mixture. As otherwise described herein, the first mixture may be formed by dry mixing MgO source compound and the metal silicate clay binder, followed by adding a stabilizer solution, for example, zirconium acetate, zirconium carbonate and/or zirconium nitrate. Other stabilizers may be provided in the solution or as a dry component with the MgO source compound and synthetic binder. In one or more alternative embodiments, the MgO source compound and/or metal silicate clay binder may be combined with the stabilizer solution without first dry mixing the MgO source compound and/or metal silicate clay binder.

The following non-limiting examples shall serve to illustrate the various embodiments of the present invention.

Examples of isomerization catalysts A-J were formed. Examples A-G and J were comparative examples, and Example I is an inventive example. The piece crush strength, fresh isomerization rate and aged isomerization rate were measured for each of isomerization catalysts A-J.

Isomerization Catalysts A and B included MgO provided in form of tablets of magnesium oxide of different purity. Both kinds of tablets were commercially produced. Isomerization catalysts A and B were substantially free of any intentionally added stabilizers or binder. Isomerization catalyst A had a diameter of about 5 mm and Isomerization catalyst B had a diameter of about 3 mm. Isomerization catalysts A and B were formed into tablets using known powder pressing methods.

Isomerization catalyst C included MgO and alumina in an amount of about 10 wt %. The composition for isomerization catalyst C was formed by adding a 20 wt. % boehmite solution in deionized water to $Mg(OH)_2$ to form an extrudable mix. The boehmite is available under the tradename DISPAL® 11N7-80 from Sasol Germany of Hamburg, Germany. The composition was extruded and had a diameter of about 3 mm. The extruded material was dried for 8 hours at 120° C. and calcined 2 hours at 500° C. in a static muffle furnace.

Isomerization catalyst D included MgO and $ZrO_2$ in an amount of about 20 wt %. The composition for isomerization catalyst D was formed by mixing a zirconium carbonate solution containing 20.3 wt % $ZrO_2$, zirconium hydroxide containing 51.7% $ZrO_2$, water and $Mg(OH)_2$ to form an extrudable mix. The $ZrO_2$ solution utilized in isomerization catalyst D is available under the tradename BACOTE® from Magnesium Elecktron Ltd. of Manchester, UK. Isomerization catalyst D was extruded and had a diameter of about 3 mm. The material was dried and calcined identical to sample C above.

Isomerization catalyst E included MgO and $SiO_2$ in an amount of about 10 wt %. The composition for isomerization catalyst E was formed by mixing a colloidal silica suspension including 30 wt % silica suspended in water with $Mg(OH)_2$ and water. Suitable colloidal silica is available under the tradename LUDOX® AS-30 from W.R. Grace and Co. of Columbia, Md., U.S.A. The composition was then extruded and had a diameter of about 3 mm. The material was dried and calcined identical to sample C above.

Isomerization catalyst F included MgO, $ZrO_2$ and $SiO_2$. $ZrO_2$ was present in an amount of about 10 wt % and $SiO_2$ was present in an amount of about 10 wt %. The composition for isomerization catalyst F was formed by mixing a Zr—O-nitrate or zirconyl nitrate solution and a colloidal silica suspension including 34 wt % silica suspended in water with $Mg(OH)_2$ to form an extrudable mix. Suitable colloidal silica suspensions are available under the tradename LUDOX®

TMA from W.R. Grace and Co. of Columbia, Md., U.S.A. The composition was then extruded and had a diameter of about 3 mm. The extruded sample was dried and calcined as sample C above.

Isomerization catalyst G included MgO, $SiO_2$ and Laponite® clay. $SiO_2$ was present in an amount of about 10 wt % and the Laponite® clay was present in an amount of about 10 wt %. The Laponite® was provided as a powder and mixed with $Mg(OH)_2$. A colloidal silica suspension including 30 wt % silica suspended in water was added with additional water to make an extrudable mix. Suitable colloidal silica is available under the tradename LUDOX® AS-30 from W.R. Grace and Co. of Columbia, Md., U.S.A. The composition was then extruded and had a diameter of about 3 mm The extrudates were dried and calcined identical to sample C above.

Isomerization catalyst H included MgO and Laponite® clay, present in an amount of about 10 wt %. Isomerization catalyst H was formed by mixing Laponite®, provided as a powder, with $Mg(OH)_2$ prior to adding water. Water was then added to the Laponite® and $Mg(OH)_2$ mixture to make an extrudable mix. The composition was then extruded and had a diameter of about 3 mm. The extrudates were dried and calcined identical to sample C above.

Isomerization catalyst I included MgO, $ZrO_2$ and Laponite® clay Isomerization catalyst I was formed by dry mixing Laponite®, provided as a powder, with $Mg(OH)_2$. A solution of zirconium carbonate containing 20.3 wt % $ZrO_2$ and additional water was added to form an extrudable mix. The $ZrO_2$ solution utilized in isomerization catalyst I is available under the tradename BACOTE® from Magnesium Elecktron Ltd. of Manchester, UK. Isomerization catalyst I was extruded and had a diameter of about 3 mm The extrudates were dried and calcined identical to sample C above.

Isomerization catalyst J included MgO, talc and $SiO_2$. Talc, colloidal silica solution containing 30 wt. % silica, $Mg(OH)_2$ and water was mixed to form an extruable mix. Suitable colloidal silica is available under the tradename LUDOX® AS-30 from W.R. Grace and Co. of Columbia, Md., U.S.A. Talc was obtained as a powder from Aldrich chemicals and added to the magnesium hydroxide powder before addition of the silica solution. The composition was then extruded and had a diameter of about 3 mm. The extrudates were dried and calcined identical to sample C above. The final composition of extrudates contained 80% MgO, 10% SiO2 and 10% talc.

The piece crush strength of each of isomerization catalysts A-J was determined by placing each catalyst between two dies having area width of 3 mm. A compressive load is applied and the force required to crush the piece was measured by a force transducer. The piece crush strength of each of isomerization catalysts A-J is shown in Table 1. Where the crush strength or fresh isomerization rate was poor, the samples were not further tested for isomerization rate.

The isomerization rate for each of isomerization select catalysts A-J was measured when each catalyst was fresh and after aging. The isomerization performance of each catalyst was measured at atmospheric pressure using 1-butene, present in an amount of 20 wt % in nitrogen, as a feed gas at 220° C. and weight hourly space velocity of 45 $h^{-1}$. The fresh isomerization performance was measured after one hour on stream. After measuring the isomerization performance of each catalyst when fresh, each of catalysts A-J were then aged by calcining at 650° C. for 24 hours in a muffle furnace. The aged performance or the performance of each of isomerization catalysts A-J were tested after aging for after 1 hour on stream. The results are provided in Table 1 and shown with the piece crush strength of each of isomerization catalysts A-J in the graph of FIG. 1.

TABLE 1

Isomerization rate and piece crush strength of isomerization catalysts A-J.

| Example | Composition | Form | Isomerization Rate (fresh) | Isomerization Rate (Aged) | Piece crush strength (lbs/mm) | Piece crush strength (kg/mm) |
|---|---|---|---|---|---|---|
| Comp. A | MgO | Tablet | 0.216 | 0.049 | 6.32 | 2.87 |
| Comp. B | MgO | Tablet | 0.699 | 0.437 | 4.84 | 2.20 |
| Comp. C | MgO—$Al_2O_3$(10%) | Extrudate | n/a | n/a | <1 | <0.45 |
| Comp. D | MgO—$ZrO_2$(20%) | Extrudate | 0.634 | 0.577 | 1.14 | 0.52 |
| Comp. E | MgO—$SiO_2$(10%) | Extrudate | 0.390 | 0.016 | 1.29 | 0.59 |
| Comp. F | MgO—$ZrO_2$(10%)—$SiO_2$(10%) | Extrudate | 0.049 | n/a | 1.67 | 0.76 |
| Comp. G | MgO—$SiO_2$(10%)-Laponite clay (10%) | Extrudate | 0.429 | 0.184 | 4.42 | 2.00 |
| Comp. H | MgO-Laponite clay (10%) | Extrudate | 0.641 | 0.137 | 2.53 | 1.15 |
| I | MgO—$ZrO_2$(10%)-Laponite clay (10%) | Extrudate | 0.682 | 0.392 | 2.99 | 1.36 |
| Comp. J | MgO-talc-$SiO_2$ | Extrudate | n/a | n/a | 1.00 | 0.45 |

As is evident from FIG. 1, isomerization catalysts containing a metal silicate clay binder (for example, isomerization catalysts G, H and I) had improved crush strength over other catalysts. In addition, isomerization catalyst I, which included both a metal silicate clay binder and a stabilizer, exhibited a fresh and aged isomerization activity that is similar to existing MgO tablets.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. An extruded catalyst comprising MgO in the range of 0.1 wt % to 90 wt %; a metal silicate clay binder in the range of 1 wt % and 20 wt % and one or more of $ZrO_2$, tetravalent rare earth metal and a trivalent rare earth metal in the range of 1 wt % and 20 wt %, the catalyst exhibiting a piece crush strength of at least 2.0 lbs/mm and exhibiting a fresh isomerization rate and an aged performance after aging at 650° C. for 24 hours, wherein the aged isomerization rate is at least 50% of the fresh isomerization rate.

2. The catalyst of claim 1, wherein MgO is present in an amount of at least 50 wt %.

3. The catalyst of claim 2, wherein MgO is present in the range from about 70 wt % to about 90 wt %.

4. The catalyst of claim 3, wherein MgO is present in an amount of about 80 wt %.

5. The catalyst of claim 1, wherein the trivalent rare earth metal comprises one or more of La, Ce, Pr and Nd.

6. The catalyst of claim 5, comprising $ZrO_2$ in an amount up to about 40 wt %.

7. The catalyst of claim 6, wherein $ZrO_2$ is present in an amount in the range from about 5 wt % to about 15 wt %.

8. The catalyst of claim 7, wherein $ZrO_2$ is present in an amount of about 10 wt %.

9. The catalyst of claim 1, wherein the metal silicate clay binder comprises layered particles having an aspect ratio of diameter to thickness in the range of 25 to 50 and strong negative charges on faces of the particles and weak positive charges on edges of the particles.

10. The catalyst of claim 9, wherein the metal silicate clay binder comprises a synthetic metal silicate.

11. The catalyst of claim 10, wherein the synthetic metal silicate clay binder comprises a synthetic hectorite.

12. The catalyst of claim 1, wherein the metal silicate clay binder is present in an amount in the range from about 5 wt % to about 20 wt %.

13. The catalyst of claim 12, wherein the metal silicate clay binder is present in an amount in the range from about 8 wt % to about 12 wt %.

14. The catalyst of claim 13, wherein the metal silicate clay binder is present in an amount of about 10 wt %.

15. The catalyst of claim 1, wherein the fresh isomerization rate and the aged isomerization rate comprise a 1-butene to 2-butene isomerization rate.

16. A method of forming a 1-butene isomerization catalyst comprising:
 mixing a MgO source, a metal silicate clay binder and one or more of a $ZrO_2$-precursor, a tetravalent rare earth metal and a trivalent rare earth metal to form a first mixture;
 adding water to the first mixture to form a second mixture; and
 extruding the second mixture to form an extrudate exhibiting a single piece crush strength of at least 2.0 lbs/mm and exhibiting a fresh isomerization rate and an aged performance after being aged at 650° C. for 24 hours, wherein the aged isomerization rate is at least 50% of the fresh isomerization rate.

17. The method of claim 16, wherein the MgO source, metal silicate clay binder and one or more of $ZrO_2$, tetravalent rare earth metal and a trivalent rare earth metal are dry-mixed.

18. The method of claim 16, wherein the one or more of $ZrO_2$, tetravalent rare earth metal and a trivalent rare earth metal is provided in solution form.

19. The method of claim 18, wherein the one or more of $ZrO_2$, tetravalent rare earth metal and a trivalent rare earth metal is selected from one of zirconium carbonate, zirconium acetate, zirconium nitrate and combinations thereof.

20. The method of claim 16, wherein metal silicate clay binder is present in an amount in the range of about 5 wt % and 20 wt %.

* * * * *